United States Patent [19]

Rajagopalan et al.

[11] Patent Number: 5,130,133
[45] Date of Patent: Jul. 14, 1992

[54] PLANT EXTRACTS AS MUCOSAL-PROTECTIVE AGENTS

[75] Inventors: Tuticorin G. Rajagopalan, Bombay, India; Jared L. Randall, North Bend, Ohio

[73] Assignee: The Procter & Gamble Company, Cincinnati, Ohio

[21] Appl. No.: 589,841

[22] Filed: Sep. 28, 1990

[51] Int. Cl.$^5$ ............................................. A61K 35/78
[52] U.S. Cl. .................................................... 424/195.1
[58] Field of Search ...................................... 424/195.1

[56] References Cited

FOREIGN PATENT DOCUMENTS 3525363 1/1987 Fed. Rep. of Germany .

OTHER PUBLICATIONS

"Effect of Ecliplá Alba on Inflammation and Liver Injury", Chandra et al.; Fitoterapia 58(1) 23–32 (1987).
"Indian Drugs", vol. 28, Issue 2, pp. 100–102, Das et al., Nov. 1990.
Bhargava, K. K. & T. R. Seshadri, "Chemistry of Medicinal Plants: Eclipta Alba and Wedelia Calendulacea", Journal of Research of Indian Medicine, vol. 9, No. 1 (1974), pp. 9–15.
Bhargava, K. K., N. R. Krishnaswamy & T. R. Seshadri, "Isolation of Desmethylwedelolactone & Its Glucoside from Eclipta Alba", Indian Journal of Chemistry, vol. 8 (1970), pp. 664–665.
Bhargava, K. K., N. R. Krishnaswamy & T. R. Seshadri, "Desmethylwedelolactone Glucoside from Eclipta Alba Leaves", Indian Journal of Chemistry, vol. 10, (Aug. 1972), pp. 810–811.
Govindachari, T. R., K. Nagarajan & B. R. Pai, "Chemical Examination of Wedelia Calendulacea, Part I, Structure of Wedelolactone", Journal of the Chemical Society (1956), pp. 629–632.
Govindachari, T. R., K. Nagarajan, B. R. Pai & P. C. Parthasarathy, "Chemical Investigation of Wedelia Calendulacea, Part II, The Position of the Methoxyl Group in Wedelolactone", Journal of the Chemical Society, (1957), pp. 545–547.
Govindachari, T. R., K. Nagarajan & P. C. Parthasarathy, "Chemical Examination of Wedelia Calendulacea, Part III, Synthesis of Tri-O-Methylwedelolactone", Journal of the Chemical Society, (1957), pp. 548–551.
Govindachari, T. R., K. Nagarajan & P. C. Parthasarathy, "Chemical Examination of Wedelia Calendulacea-IV, Synthetic Analogues of Wedelolactone", Tetrahedron, vol. 15 (1961), pp. 129–131.
Govindachari, T. R. & M. S. Premila, "Benzofuran Norwedelic Acid from Wedelia Calendulacea", Phytochemistry, vol. 24, No. 12 (1985), pp. 3068–3069.
Handa, S. S., P. Prakash & B. Roy, "Bioactivity Directed Extraction and Fractionation of Eclipta Alba-an Antihepatotoxic Drug of Indian Origin", Indian Journal of Pharmaceutical Sciences, (Jan.–Feb., 1984), p. 50 (abstract only).
Krishnaswamy, N. R., T. R. Seshadri & B. R. Sharma, "The Structure of a New Polythinyl from Eclipta Alba", Tetrahedron Letters, No. 35 (1966), pp. 4227–4230.
Wagner, H., B. Geyer, Y. Kiso, H. Hikino & G. S. Rao, "Coumestans as the Main as the Main Active Principles of the Liver Drugs Eclipta Alba and Wedelia Calendulacea:", Planta Medica, vol. 5 (1986), pp. 370–374.
Wagner, H. & B. Fessler, "In–Vitro–5–Lipoxygenasehemmung Durch Eclipta Alba Extrakte and das Coumestan–Derivat Wedelolacton", Planta Medica, (1986), No. 5, No. 5, pp. 374–377.
Yang, L.-L., K.-Y. Yen, C. Konno, Y. Oshima, Y. Kiso & H. Hikino, "Antiheptaotoxic Principles of Wedelia Chinensis Herbs", Planta Medica (1986), No. 6, pp. 499–500.
"Chimpanzees Guide Researchers to New Antibiotic", American Pharmacy, vol. NS26, No. 3 (Mar. 1986), p. 13.
Farouk, A., A. K. Bashir & A. K. M. Salih, "Antimicrobial Activity of Certain Sudanese Plants Used in Folkloric Medicine, Screening for Antibacterial Activity (I)", FTRPAE, Fitoterapia, vol. 54, Issue 1 (1983), pp. 3–7.
Rodriguez, E., M. Aregullin, T., Nishida, S. Uehara, R. Wrangham, Z. Abramowski, A. Finlayson & G. H. N. Towers, "Thiarubrine A, a Bioactive Constituent of Aspilia (asteraceae) Consumed by Wild Chimpanzees", Experientia, vol. 41, (1985), pp. 419–420.
Rogue, N. F., T. L. Giannella, A. M. Giesbrecht & R. Barbosa, "Kaurene Diterpenes Wedelia Paludosa", Rev. Latinoamer, Quim., vol. 18, No. 3 (1987), pp. 110–111.

Primary Examiner—John W. Rollins
Attorney, Agent, or Firm—Milton B. Graff, IV; Jerry J. Yetter; Richard C. Witte

[57] ABSTRACT

The subject invention relates to methods for providing mucosal-protection comprising administering to a human or lower animal a safe and effective amount of an extract from plant species of the genera Wedelia, Eclipta and Aspilia.

20 Claims, No Drawings

PLANT EXTRACTS AS MUCOSAL-PROTECTIVE AGENTS

TECHNICAL FIELD

The subject invention relates to extracts of tissues of certain plant species from the genera Wedelia, Eclipta and Aspilia which are effective as gastrointestinal mucosal-protective agents.

BACKGROUND OF THE INVENTION

Various species from the genera Wedelia, Eclipta and Aspilia have been disclosed to have a variety of different biological or pharmacological activities.

Two frequently studied species of these genera are *Wedelia calendulaceae* and *Eclipta alba*. The most common medicinal use of extracts from these plants is for treatment of liver ailments. For this use, the active compounds found in these species are believed to be coumestans, especially wedelolactone and related compounds. Extracts from these plants have also been used to treat a number of other ailments such as catarrh, skin diseases, elephantiasis, toothaches and headaches, as well as being used as emetic and purgative materials, and as external antiseptics. Shoot extracts have been shown to have antibiotic activity against certain species. The following references disclose activities of extracts of *W. calendulacea* and *E. alba*, methods for obtaining extracts from them, and active components isolated from the extracts: Bhargava, K. K & T. R. Seshadri, "Chemistry of Medicinal Plants: *Eclipta alba* and *Wedelia calendulacea*", *Journal of Research of Indian Medicine*, Vol. 9, No. 1 (1974), pp. 9–15; Wagner, H., B. Geyer, Y. Kiso, H. Hikino & G. S. Rao, "Coumestans as the Main Active Principles of the Liver Drugs *Eclipta alba* and *Wedelia calendulacea*", *Planta Medica*, Vol. 5 (1986), pp. 370–374; Handa, S. S., P. Prakash & B. Roy, "Bioactivity Directed Extraction and Fractionation of *Eclipta alba*—an Antihepatotoxic Drug of Indian Origin", *Indian Journal of Pharmaceutical Sciences*, (Jan.-Feb., 1984), p. 50 (abstract only); Govindachari, T. R., K. Nagarajan & B. R. Pai, "Chemical Examination of *Wedelia calendulacea*. Part I. Structure of Wedelolactone", *Journal of the Chemical Society*, (1956), pp. 629–632; Govindachari, T. R., K. Nagarajan, B. R. Pai & P. C. Parthasarathy, "Chemical Investigation of *Wedelia calendulacea*. Part II. The Position of the Methoxyl Group in Wedelolactone", *Journal of the Chemical Society*, (1957), pp. 545–547; Govindachari, T. R., K. Nagarajan & P. C. Parthasarathy, "Chemical Examination of *Wedelia calendulacea*. Part III. Synthesis of Tri-O-methylwedelolactone", *Journal of the Chemical Society*, (1957), pp. 548–551; Govindachari, T. R., K. Nagarajan & P. C. Parthasarathy, "Chemical Examination of *Wedelia calendulacea*-IV Synthetic Analogues of Wedelolactone", *Tetrahedron*, Vol. 15 (1961), pp. 129–131; Govindachari, T. R. & M. S. Premila, "The Benzofuran Norwedelic Acid from *Wedelia calendulacea*", *Phytochemistry*, Vol. 24, No. 12 (1985), pp. 3068–3069; Bhargava, K. K., N. R. Krishnaswamy, & T. R. Seshadri, "Isolation of Desmethylwedelolactone & Its Glucoside from *Eclipta alba*", *Indian Journal of Chemistry*, Vol. 8 (1970), pp. 664–665; Bhargava, K. K, N. R. Krishnaswamy & T. R. Seshadri, "Desmethylwedelolactone Glucoside from *Eclipta alba* Leaves", *Indian Journal of Chemistry*, Vol 10 (Aug., 1972), pp. 810–811; Wagner, H. & B. Fessler, "In-Vitro-5-Lipoxygenasehemmung durch *Eclipta alba* Extrakte und das Coumestan-Derivat Wedelolacton", *Planta Medica*. (1986), No. 5, pp. 374–377; Krishnaswamy, N. R., T. R. Seshadri & B. R. Sharma, "The Structure of a New Polythienyl from *Eclipta alba*", *Tetrahedron Letters*, No. 35 (1966), pp. 4227–4230; and German Patent Application No. DE3,525,363 of Medice Chem.-pharm. Fabrik Putter GmbH & Co. KG, Inventor H. Wagner, published Jan. 22, 1987.

Antihepatotoxic activity has also been reported for an extract from the plant *Wedelia chinensis*: Yang, L.-L., K.-Y. Yen, C. Konno, Y. Oshima, Y. Kiso & H. Hikino, "Antihepatotoxic Drugs. Part 32. Antihepatotoxic Principles of *Wedelia chinensis* Herbs", *Planta Medica* (1986), No. 6, pp. 499–500. Antibacterial activity has also been discovered in extracts from other plants of the genera Wedelia. Eclipta and Aspilia: Roque, N. F., T. L. Giannella, A. M. Giesbrecht & R. Barbosa, "Kaurene Diterpenes from *Wedelia paludosa*", *Rev. Latinoamer. Quim.*, Vol 18, No. 3 (1987), pp. 110–111; Farouk, A., A. K. Bashir & A. K. M. Salih, "Antimicrobial Activity of Certain Sudanese Plants used in Folkloric Medicine. Screening for Antibacterial Activity (I)", *FTRPAE, Fitoterapia*, Vol. 54, Issue 1 (1983), pp. 3–7; Rodriguez, E., M. Aregullin, T. Nishida, S. Uehara, R. Wrangham, Z. Abramowski, A. Finlayson & G. H. N. Towers, "Thiarubrine A, a Bioactive Constituent of Aspilia (Asteraceae) consumed by Wild Chimpanzees", *Experientia*, Vol. 41 (1985), pp. 419–420; and "Chimpanzees Guide Researchers to New Antibiotic", *American Pharmacy*, Vol. NS26, No. 3 (Mar., 1986), p. 13.

It is an object of the subject invention to provide novel compositions having mucosal-protective activity.

It is another object of the subject invention to provide novel methods for treating or preventing gastrointestinal maladies such as gastritis, non-ulcer dyspepsia, gastroesophageal reflux disease, esophagitis, gastric ulcers, duodenal ulcers, gastric cancer, Zollinger-Ellison syndrome, ethanol-induced damage, non-steroidal anti-inflammatory drug (NSAID)-induced damage, ileitis, Crohn's disease, colitis, ulcerative colitis, and inflammatory bowel disease.

It is also an object of the subject invention to provide novel processes for obtaining extracts from certain plant species having mucosal-protective activity.

SUMMARY OF THE INVENTION

The subject invention relates to methods for providing mucosal protection in the gastrointestinal tract comprising administering to a human or lower animal a safe and effective amount of an extract from certain plant species of the genera Wedelia, Eclipta and Aspilia.

DETAILED DESCRIPTION OF THE INVENTION

The subject invention involves extracts from the tissues of certain plant species which provide mucosal-protective activity against gastrointestinal disorders of the upper and lower gastrointestinal tract. As used herein, "upper gastrointestinal" refers to the esophagus, the stomach and the duodenum. As used herein, "lower gastrointestinal" refers to the jejunum, the ileum and the colon. As used herein, "mucosal-protective" means mucosal-protective in the gastrointestinal tract.

As used herein, upper gastrointestinal disorders which can be treated or prevented by administration of compositions comprising the extracts of the subject invention include gastritis, non-ulcer dyspepsia, gastroesophageal reflux disease, esophagitis, gastric ulcers, duodenal ulcers, gastric cancer, Zollinger-Ellison syndrome, ethanol-induced damage and NSAID-induced damage. The compositions of the subject invention are particularly useful for treatment of gastritis, gastric ulcers, duodenal ulcers, non-ulcer dyspepsia, ethanol-induced damage and NSAID-induced damage, especially gastritis, non-ulcer dyspepsia and NSAID-induced damage. The compositions of the present invention are particularly useful for prophylactic protection from gastric ulcers, ethanol-induced damage and NSAID-induced damage, especially NSAID-induced damage.

As used herein, lower gastrointestinal disorders which can be treated or prevented by administration of compositions comprising the extracts of the subject invention include ileitis, Crohn's disease, colitis, ulcerative colitis, and inflammatory bowel disease. The compositions of the subject invention are particularly useful for treatment of regional and erosive stages of ileitis, colitis and inflammatory bowel disease, especially inflammatory bowel disease.

Extracts of the subject invention which are useful for the treatment of gastrointestinal disorders of the upper gastrointestinal tract are obtained from species of the genera Wedelia, Eclipta and Aspilia; preferred species from which such extracts are obtained include *A. floribunda, A. paryifloia, E. alba, E. erecta, E. prostrate, W. asperrima, W. biflora, W. buphthalmiflora, W. calendulacea, W. calycina, W. chinesis, W. forsteriana, W. glauca, W. grandiflora, W. helianthoides, W. ispida, W. hookeriana, W. keatingii, W. paludosa, W. parviceps, W. pinetorum, W. scaberrima and W. trilobata*. Particularly preferred are extracts from *E. alba* and especially *W. calendulacea*.

Extracts from the above plant species which are included in the subject invention are those which have mucosal-protective activity. It has been found that a wide variety of extraction solvents can be used to obtain extracts of these plant species having mucosal-protective activity. As used herein, "mucosal-protective activity" of an extract or composition can be determined using the following procedure.

Test Method

Animals: Adult male rats (CD strain) weighing 185 to 195 grams each are purchased from Charles River Breeding Laboratories (Portage, Mich.). Upon receipt, rats are double-housed in stainless steel mesh-bottom cages with access to automatic water and Purina rat chow in the form of pellets. The animal room is maintained at 20°-23° C. and 50-60% relative humidity with a twelve hour light/dark cycle. Animals are allowed to acclimate for 7 days prior to use.

To prevent coprophagy, 18 to 24 hours prior to the experiment, cups are affixed to tails with Eastman 910 glue. At the time of tailcupping, rats are weighed, single housed and food fasted with water ad libitum. Unfasted body weights of rats used in experiments range from 225 to 295 grams. One to two hours prior to experiment, the water line is unhooked from the animal rack and the lines drained.

Dose Solution Preparation: Appropriate weights of extract and distilled deionized water are shaken or stirred magnetically. When necessary, the pH of the solution is adjusted with either sodium hydroxide or hydrochloric acid to near neutrality (pH 5 to 7.5). Solutions are stirred magnetically while dosing.

Assay for Ethanol-Induced Gastric Damage: All solutions (water only for Control Group) are dosed orally into the stomach with a small nethalon catheter (8 French) fitted onto a disposable plastic syringe. Dose volume for treatments and ethanol is 1 mL/rat. Ethanol is dosed orally 60 minutes after treatments and rats are sacrificed by cervical dislocation 60 minutes after ethanol administration. Stomachs are dissected, cut along the greater curvature and placed into scintillation vials containing 8-10 mL of 0.9% saline. Approximately 30 to 90 minutes later, stomachs are placed with the mucosal side facing up on numbered cards and damage is observed under a microscope at low power (10×). A Zeiss Zidas Digitizing Pad is used to measure damage. Total length (mm) of lesions for each rat is automatically tabulated by the digitizer.

Statistics: Group statistics are calculated on a computerized spreadsheet. The mean of the total lesion length (mm) for the rats ("Mean Lesions") is calculated for each treatment group and the control group. Percent protection is determined as follows: $1-$(Treatment Group Mean Lesions/Control Group Mean Lesions)$\times 100$. One-way analysis of variance, followed by LSD test, is used to determine differences between treatments (p $0.05=$significantly different).

Extracts of the subject invention may be obtained from a variety of tissues from the above-identified plant species. Extracts from the above-ground tissues of the plants are preferred, especially from the leaves. Extracts may be made from fresh plant tissues, or from the tissues after they are dried. Preferred are extracts of dried leaves.

As used herein, "extracting" or "extraction" of a solid or liquid material means contacting the material, which if solid is preferably dried and crushed or ground, with an appropriate solvent to remove the substance(s) desired to be extracted from the material. Such an extraction may be carried out by conventional means; for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

Preferred extracts of the subject invention are made from defatted plant tissues, especially defatted dried leaves. Defatted plant tissues can be prepared by extracting the plant tissues using an appropriate solvent. Preferred solvents include methylene chloride, hexane, pentane, petroleum ether, chloroform and ethylene dichloride, especially methylene chloride. Preferably, 1 part of plant tissue (dry basis) is extracted with from about 5 to about 50 parts, preferably from about 15 parts to about 30 parts of solvent using an extraction apparatus where the solvent is refluxed through the tissues for a long period of time, preferably from about 6 hours to about 7 days, more preferably for about 1-4 days. The defatted plant tissues are preferably dried prior to further extraction steps.

The subject invention includes a process for preparing a weak acid extract of tissues of the plants of interest, preferably of leaves, especially dried leaves, by extracting the tissues with an aqueous acid solution having a pH of from about 1.5 to about 5, preferably from about 2 to about 4, more preferably from about 2.5 to about 3.5. Preferred weak acids include malic, formic, lactic, tartaric, acetic and citric, and also include dilute strong acids such as sulfuric and hydrochloric. Preferred is acetic acid. Also preferred are natural juices which are weak acids, such as citric juices, especially lemon juice. Preferably, part of plant tissues (dry basis) is extracted using from about 5 to about 20 parts, preferably from about 8 to about 10 parts of aqueous acid solution, the solution preferably being from about 1% to about 5%, more preferably about 2%, acid. A mixture of the tissues and acetic acid solution is preferably stirred for from about 2 to about 24 hours, preferably for from about 3 to about 5 hours. The resulting liquid extract is separated from the plant tissue residue. The liquid extract is preferably dried by conventional means such as by rotary evaporation, freeze drying or spray drying, to provide a solid weak acid extract.

The subject invention includes a process for preparing a weak acid extract of tissues of the plants of interest, by extracting the tissues with lemon juice. The tissues of plants preferably extracted are the leaves; especially preferred is extracts of dried leaves. Preferably, 1 part of plant tissues (dry basis) is extracted using from about 1 to about 10 parts, preferably from about 2 to about 3 parts of lemon juice, preferably freshly squeezed, and preferably with from about 5 to about 20 parts, more preferably from about 8 to about 10 parts of water. The mixture is preferably stirred for from about 2 to about 24 hours, more preferably for from about 3 to about 5 hours. The resulting liquid extract is separated from the plant tissue residue. The liquid extract is preferably dried by conventional means, such as by evaporation, freeze drying or spray drying to provide a solid lemon juice extract.

The subject invention includes a process for preparing an alcohol extract of tissues of the plants of interest, preferably of leaves, especially dried leaves, by extracting the tissues using water-miscible alcohol, such as methanol, ethanol, n-propanol or ispropanol or mixtures of such alcohols with up to about 50% water; the preferred alcohol is methanol. Preferably, 1 part of plant tissues (dry basis) is extracted with from about 5 to about 50 parts, more preferably from about 15 to about 30 parts of solvent, using an extraction apparatus, where the solvent is refluxed thru the tissues, for a period of from about 4 to about 48 hours, preferably for from about 12 to about 24 hours. The alcohol is preferably evaporated from the resulting liquid alcohol extract, that providing a solid alcohol extract. The alcohol extract may optionally be acid treated by dissolving it in acid and separating out any solid residue. For example, the alcohol extract is mixed with an acid solution, preferably a weak acid solution such as 0.1 N HCl. Preferably, 1 part of solid alcohol extract is mixed with from about 10 to about 1000 parts, more preferably about 100 parts of acid solution. Residual solids are separated from the solution, preferably by filtration. The filtrate is neutralized, preferably with a weak base such as 0.1 N NaOH. Water is preferably evaporated from the resulting solution to provide solid acid-treated alcohol extract.

The subject invention includes a process for preparing a 1-butanol extract from an alcohol extract (an alcohol/1-butanol extract). This process comprises dissolving the alcohol extract (optionally defatted and optionally acid treated) in water and extracting with 1-butanol. The resulting liquid 1-butanol extract is separated from the remaining water phase, and preferably the 1-butanol is evaporated from the liquid 1-butanol extract to provide a solid 1-butanol extract. In this process, preferably, 1 part of alcohol extract (dry basis) is dissolved in from about 30 to about 300 parts, more preferably from about 100 to about 150 parts of water. The resulting aqueous solution is preferably mixed with from about 0.1 to about 2 parts, more preferably about 0.5 parts of 1-butanol. Preferably the 1-butanol extraction is carried out in from about 1 to about 4 steps, more preferably about 2 steps, by dividing the quantity of 1-butanol into about equal portions and separately mixing each portion of 1-butanol with the alcohol extract solution and then separating the 1-butanol phase from the aqueous phase. The 1-butanol portions are combined to provide a liquid 1-butanol extract, and preferably the 1-butanol is evaporated to provide a solid 1-butanol extract. During evaporation of the 1-butanol, when most of the 1-butanol is evaporated, water is preferably added, followed by further evaporation to remove the residual 1-butanol. The aqueous solution is then preferably dried to obtain the solid 1-butanol extract.

Freeze drying is a preferred method for drying aqueous solutions in the above processes.

The following are examples of extraction processes used for obtaining extracts of the subject invention. They are not intended to be limiting with regard to extraction procedures that can be used.

EXAMPLE 1

Preparation of Leaf Powders Used in Extraction Procedures

Dried leaves are obtained from one or more desired Wedelia, Eclipta and/or Aspilia species. The dried leaves are crushed with a mortar and pestle, or with a ball-mill apparatus. The powdered material obtained is passed through a 60-mesh screen. The 60-mesh powder obtained is used in the extraction procedures.

EXAMPLE 2

Preparation of Lemon Juice Extract

Powdered leaves (100 g) from Example 1, freshly squeezed lemon juice (150 mL), and distilled water (900 mL) are added to a 2-L round-bottom flask. The mixture obtained is stirred with a mechanical stirrer for 4 hours. Filtration of the dark green mixture through muslin cloth provides a turbid, dark green solution. A portion of the solution (450 mL) is spray-dried to provide a tan-green lemon juice extract powder (13.9 g). Another portion (200 mL) is freeze-dried to provide a tan-green lemon juice extract powder (5.85 g).

EXAMPLE 3

Preparation of Acetic Acid Extract

Powdered leaves (100 g) from Example 1, acetic acid (18 mL), and distilled water (900 mL) (provides a 2% aqueous acetic acid solution) are added to a 2-L round-bottom flask. The mixture obtained is stirred with a mechanical stirrer for 4 hours. Filtration of the dark green mixture through muslin cloth provides a turbid, dark green solution. The solution is freeze-dried to provide a dark green acetic acid extract solid (17 1 g).

EXAMPLE 4

Preparation of Defatted Acetic Acid Extract

Powdered leaves (50 g) from Example 1 are placed in an extraction thimble which is then placed in a Soxhlet extraction apparatus. Methylene chloride (1.5 L) is added to the distillation pot of the Soxhlet apparatus and the solvent is refluxed through the extraction thimble for 24 hours. The defatted leaf residue is removed, dried in air (4 hours), and then dried in vacuo (8 hours). The dried residue and 3% aqueous acetic acid (1.5 L) are added to a 2-L round-bottom flask. The mixture obtained is stirred with a mechanical stirrer for 18 hours. Filtration of the dark green mixture through muslin cloth provides a turbid, dark green solution. The acetic acid in the solution is largely evaporated on a rotary evaporator, and the remaining aqueous solution is freeze-dried to provide a dark green defatted acetic acid extract solid (5.4 g).

EXAMPLE 5

Preparation of Methanol Extract

Powdered leaves (50 g) from Example 1 are placed in an extraction thimble which is then placed in a Soxhlet extraction apparatus. Methanol (1.5 L) is added to the distillation pot of the Soxhlet apparatus and the solvent is refluxed through the extraction thimble for 12 hours. The methanol solution is evaporated on a rotary evaporator, and the dark gummy residue obtained is dried in vacuo. The dark green solid obtained is crushed to provide a methanol extract powder (3.7 g).

EXAMPLE 6

Preparation of Defatted-Methanol Extract

Powdered leaves (100 g) from Example 1 are placed in an extraction thimble which is then placed in a Soxhlet extraction apparatus. Methylene chloride (1.5 L) is added to the distillation pot of the Soxhlet apparatus and the solvent is refluxed through the extraction thimble for 24 hours. The defatted leaf residue is removed, dried in the air (4 hours), and then dried in vacuo (8 hours). The dried residue is placed in an extraction thimble which is then placed in a Soxhlet extraction apparatus. Methanol (1.5 L) is added to the distillation pot of the Soxhlet apparatus and the solvent is refluxed through the extraction thimble for 24 hours. The methanol solution is evaporated on a rotary evaporator, and the dark residue obtained is dried in vacuo. The dark green solid obtained is crushed to provide a defatted methanol extract powder (14.3 g).

EXAMPLE 7

Preparation of Acid-Treated, Defatted, Methanol Extract

The defatted methanol extract powder (2 g) of Example 6 is added to an aqueous 0.1N HCl solution (200 mL) and magnetically stirred (5 minutes). The precipitate which forms is removed by filtration and the filtrate is neutralized with an aqueous 0.1N NaOH solution. The solution is freeze-dried to provide a defatted acid-treated methanol extract solid (980 mg).

EXAMPLE 8

Preparation of Defatted 1-Butanol Extract

The defatted methanol extract powder (3.25 g) of Example 6 is dissolved in distilled water (400 mL) and extracted with 1-butanol (2×100 mL). The 1-butanol portions are evaporated on a rotary evaporator. When most of the 1-butanol is evaporated, water (100 mL) is added to the evaporating flask which is again placed on the rotary evaporator to remove the residual 1-butanol. The aqueous solution which remains is freeze-dried to obtain a defatted 1-butanol extract solid (0.72 g).

EXAMPLE 9

Preparation of Defatted Acid-Treated 1-Butanol Extract

Powdered leaves (133 g) from Example 1 are placed in an extraction thimble which is then placed in a Soxhlet apparatus. Methylene chloride (1 L) is placed in the distillation pot of the apparatus and the leaf material is continuously extracted for 4 days. The leaf residue is removed from the extraction apparatus and dried in air and then in vacuo. The dried leaf material (115 g) is placed in an extraction thimble which is then placed in a Soxhlet extraction apparatus. Methanol (1.5 L) is added to the distillation pot of the Soxhlet apparatus and the solvent is refluxed through the extraction thimble for 4 days. The methanol solution is evaporated on a rotary evaporator, and the dark residue obtained is dried in vacuo. The dark green solid obtained is crushed to provide defatted methanol extract powder (14.3 g). This extract is then added to 0.1 N HCl aqueous solution (600 mL) and magnetically stirred (20 minutes). The solution is placed into vessels which are centrifuged at 5 G. After 10 minutes, the supernatant is removed and the pH is adjusted to 7.8 by the addition of 0.1 N NaOH solution. The aqueous solution is then extracted once with 1-butanol (300 mL). The 1-butanol solution obtained is combined with water (250 ml) and evaporated on a rotary evaporator. When most of the 1-butanol is evaporated, water (100 mL) is added to the evaporating flask which is again placed on the rotary evaporator to remove the residual 1-butanol. The aqueous solution obtained is freeze-dried to provide a defatted acid-treated 1-butanol extract solid (3.37 g).

EXAMPLE 10

Preparation of Defatted n-Propanol:Water 1-Butanol Extract

Powdered leaves (50 g) from Example 1 are placed in a 3-speed blender with a speed of 18,000 rpm and blended with 5×300 mL n-propanol:distilled water (7:3), 20 seconds at a stretch, five times with every 300 mL n-propanol:distilled water (7:3) added. The mixture is filtered through a G-1 sintered funnel. Filtration of this mixture provides a dark green solution. The n-propanol is largely evaporated on a rotary evaporator and the remaining aqueous solution is extracted with 1×200 mL and further 2×100 mL hexane for defatting. The aqueous fraction is further extracted with 4×100 Ml water-saturated 1-butanol. The 1-butanol is evaporated on a rotary evaporator and the dark, gummy residue is dried in vacuo. The dark green solid obtained is crushed to provide a defatted 1-butanol extract (10 g).

Another aspect of the subject invention involves compositions comprising an extract of the subject invention, such as described hereinabove, and a pharmaceutically-acceptable carrier. Preferred compositions are those in dosage forms intended for oral administration. Fluid dosage forms for oral administration include solutions, suspensions, emulsions, and the like.

Solid dosage forms for oral administration include tablets, capsules, powders, lozenges, and the like.

The term "pharmaceutically-acceptable carrier" as used herein means one or more compatible solid or liquid filler diluent or encapsulating substance which is suitable for administration to a human or lower animal. The term "compatible" as used herein means that the components of the pharmaceutical carrier are capable of being commingled with the extracts of the subject invention, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch, cellulose and its derivatives, such as sodium carboxymethylcellulose, ethylcellulose, cellulose acetate; powdered tragacanth; malts; gelatin; talc; steric acid; magnesium stearate; calcium sulfate; vegetable oil such peanut oil, cottonseed oil, sesame oil, olive oil, corn oil and oil of theobroma; polyols such as propylene glycol, glycerine, sorbitol, mannitol, and polyethylene glycol; alginic acid; purified water; emulsifiers, such as the Tweens ®; as well as other non-toxic compatible substances used in the pharmaceutical formulation. Wetting agents and lubricants such as sodium lauryl sulfate, as well as coloring agents, flavoring agents, excipients, tableting agents, stabilizers, anti-oxidants, and preservatives, can also be present.

The following are Examples of compositions of the subject invention. They are not intended to be limiting with regard to useful compositions that can be prepared from the extracts of the subject invention.

EXAMPLE 11

Capsules

The spray-dried powder lemon juice extract of Example 2 is used to prepare capsules by blending 2 parts of the extract with 1 part sucrose and granulating by adding ethanol and blending. The wet granules are dried and passed through a 22-mesh screen; fines are removed with a 30-mesh screen. Hard gelatin capsule shells are filled with 550 mg of granules in each capsule using conventional means.

EXAMPLE 12

Coated Granules

The dried, powdered acetic acid extract of Example 4 is granulated by blending 6 parts of the powdered extract with 13 parts sucrose and 1 part sodium chloride. These materials are passed through a 40-mesh screen and ethanol is added as the granulating agent. The granules are passed through a 22-mesh screen and dried. Fines are removed with a 30-mesh screen. The granules are transferred to a coating pan and coated initially with 18 parts of a 5% hydroxypropylmethyl cellulose solution (the solvent being a 2:1 mixture of dichloromethane: ethanol) with intermittent addition of 0.14 part of peppermint oil flavor. The granules are then coated with 14 parts of a 2.5% hydroxypropylmethyl cellulose solution followed by drying. The granules are passed through a 16-mesh screen and fines are removed with a 30-mesh screen. The retained granules are packed into sachets.

EXAMPLE 13

Tablets

The dried, powdered 1-butanol extract of Example 9 is granulated by blending 6 parts with 13 parts sucrose and 1 part sodium chloride, and using ethanol as the granulating liquid. The granules are passed through a 16-mesh screen and dried; fines are removed with a 44-mesh screen. 100 Parts granules are blended with 2 parts talc and 1 part magnesium stearate. This mixture is compressed into 1-gram tablets by conventional means.

Another aspect of the subject invention includes methods for treating or preventing gastrointestinal disorders in humans or lower animals by administering, to a human or lower animal in need of such treatment or prevention, a safe and effective amount of an extract or a composition of the subject invention. This safe and effective amount can be given in a single dose or multiple doses repeatedly over the course of the treatment. Preferred methods of administering the compositions of the subject invention include peroral, intraperitoneal, or directly (e.g., by tube) to the afflicted part of the gastrointestinal tract, especially peroral.

The phrase "safe and effective amount", as used herein, means an amount of the composition of the subject invention high enough to significantly modify the condition to be treated in a positive way, but low enough to avoid serious side effects (at a reasonable benefit/risk ratio), within the scope of sound medical judgement. The safe and effective amount of a composition will vary with the particular condition being treated, the age and physical condition of the patient being treated, the severity of the condition, the duration of treatment, the nature of concurrent therapy, the specific composition employed, the particular pharmaceutically-acceptable carrier utilized, and like factors within the knowledge and expertise of the attending physician.

The methods of the subject invention include treatment of humans and lower animals, especially humans, currently suffering from one or more upper or lower gastrointestinal disorders, particularly those specified hereinbefore, in order to reduce the severity of the disorder. The methods of the subject invention also include the prevention of upper or lower gastrointestinal disorders in humans and lower animals, especially humans, having a propensity for such disorders, particularly those specified hereinbefore, by prophylactic treatment in order to prevent occurrence of the disorder.

The methods of the subject invention include administering to a human or lower animal a composition comprising an extract of the subject invention. The quantity of extract (dry basis) administered is preferably from about 1 mg/kg to about 1000 mg/kg of body weight, more preferably from about 5 mg/kg to about 500 mg/kg, more preferably still from about 10 mg/kg to about 200 mg/kg. These quantities of extract are preferably administered from about 1 to about 4 times daily, more preferably 2 or 3, or especially about 4 times daily. The extract is preferably administered from about 0 to about 2 hours before meals, more preferably from about ½ hour to about 1 hour before meals.

The extracts of the subject invention have a rapid onset of action, and are particularly suitable for treatment of occasional gastrointestinal disorders, such as gastritis, non-ulcer dyspepsia and gastroesophageal reflux disease, as needed. Such disorders are preferably treated using a composition, such that the extract of the subject invention is dosed at a level of from about 1 mg/kg to about 1000 mg/kg, more preferably from about 5 mg/kg to about 500 mg/kg, more preferably still from about 10 mg/kg to about 200 mg/kg, as needed at the onset or during symptomatic episodes of such disorders. If the symptoms persist, additional doses are preferably administered at intervals of from about 1 to about 6 hours, more preferably at intervals of about 2 or 3 or 4 hours.

For prophylactic protection of gastrointestinal disorders, especially NSAID-induced damage, it is preferred that the compositions of the subject invention be administered from 0 to about 6 hours, more preferably from about ¼ hour to about 3 hours, more preferably still from about ½ hour to about 1 hour, prior to administration of the NSAID. For such prophylactic protection, preferred doses of extracts of the subject invention are from about 1 mg/kg to about 1000 mg/kg, more preferably from about 5 mg/kg to about 500 mg/kg, more preferably still from about 10 mg/kg to about 200 mg/kg.

The following are examples of preventing or treating gastrointestinal disorders according to the subject invention. They are not intended to be limiting with regard to methods included within the scope of the invention.

EXAMPLE 14

A person afflicted with colitis ingests 1 capsule of Example 11 every 8 hours for 7 days to obtain relief from the symptoms of the disease.

EXAMPLE 15

A person afflicted with gastritis ingests 1 gram of the granulus of Example 12 to obtain rapid relief from the gastritis symptoms.

EXAMPLE 16

A person determined to be at high risk of developing a gastric ulcer ingests 1 of the tables of Example 13 daily for 6 months to prevent the occurrence of an ulcer.

While particular embodiments of the subject invention have been described, it will be obvious to those skilled in the art that various changes and modifications to the compositions and methods disclosed herein can be made without departing from the spirit and scope of the invention. It is intended to cover, in the appended claims, all such modifications that are within the scope of this invention.

What is claimed is:

1. A method for treating or preventing gastrointestinal disorders selected from the group consisting of gastritis, non-ulcer dyspepsia, gastroesophageal reflux disease, esophagitis, gastric ulcers, duodenal ulcers, ethanol-induced damage, non-steroidal anti-inflammatory drug (NSAID)-induced damage, ileitis, Crohn's disease, colitis, ulcerative colitis, and inflammatory bowel disease in humans and lower animals by administering, to humans and lower animals in need of such treatment or prevention, a safe and effective amount of an extract of defatted tissues of a plant selected from the genera Wedelia, Eclipta and Aspilia.

2. The method of claim 1 wherein the plant is selected from the following group of species: *A. floribunda, A. parvifloia, E. alba, E. erecta, E. prostrata, W. asperrima, W. biflora, W. buphthalmiflora, W. calendulacea, W. calycina, W. chinesis, W. forsteriana, W. glauca, W. grandiflora, W. helianthoides, W. hispida, W. hookeriana, W. keatingii, W. paludosa, W. parviceps, W. pinetorum, W. scaberrima* and *W. trilobata*; the plant tissue from which the extract is taken comprises the leaves of the plant; and the quantity of extract administered is from about 1 mg/kg to about 1000 mg/kg of body weight from about 1 to about 4 times a day.

3. The method of claim 2 wherein the plant species is *E. alba*; and the quantity of extract administered is from about 5 mg/kg to about 500 mg/kg.

4. The method of claim 2 wherein the plant species is *W. calendulacea*; and the quantity of extract administered is from about 5 mg/kg to about 500 mg/kg.

5. The method of claim 3 wherein the extract is obtained by using an extracting solution selected from the group consisting of an aqueous weak acid solution having a pH of from about 1.5 to about 5, a water-miscible alcohol, and a water-miscible alcohol/1-butanol.

6. The method of claim 4 wherein the extract is obtained by using an extracting solution selected from the group consisting of an aqueous weak acid solution having a pH of from about 1.5 to about 5, a water-miscible alcohol, and a water-miscible alcohol/1-butanol.

7. The method of claim 6 wherein the extract is a methanol/1-butanol extract.

8. The method of any of claims 2–4 wherein the gastrointestinal disorder is an upper gastrointestinal disorder.

9. The method of any of claims 5–7 wherein the method is for treatment of a gastrointestinal disordered selected from the group consisting of gastritis, non-ulcer dyspepsia and NSAID-induced damage.

10. The method of any of claims 5–7 wherein the method is for prophylactic protection from gastrointestinal disorders selected from the group consisting of gastric ulcers, ethanol-induced damage and NSAID-induced damage.

11. A lemon juice extract of defatted plant tissues, the tissues comprising the leaves of a plant selected from the group of plant genera consisting of Wedelia, Eclipta and Aspilia.

12. A composition comprising from about 1% to about 95% of the extract of claim 11, wherein the plant species is *W. calendulacea*; and from about 5% to about 99% of a pharmaceutically-acceptable carrier.

13. A water-miscible alcohol/1-butanol extract of defatted plant tissues, the tissues comprising the leaves of a plant selected from the group of plant genera consisting of Wedelia, Eclipta and Aspilia.

14. A composition comprising from about 1% to about 95% of the extract of claim 13, wherein the plant species is *W. calendulacea*; and from about 5% to about 99% of a pharmaceutically-acceptable carrier.

15. The composition of claim 14 wherein the extract is a methanol/1-butanol extract.

16. A process for preparing a lemon juice extract of plant tissues, wherein the plant tissues comprise leaves of a plant selected from the group of plant genera consisting of Wedelia, Eclipta and Aspilia, the process comprising the following steps:

(a) defatting the plant tissues by extracting the tissues using a defatting solvent;

(b) extracting the defatted plant tissues with lemon juice using at least 1 part lemon juice to one part plant tissues; and (c) optionally drying the resulting liquid extract.

17. The process of claim 16 wherein the plant species is *W. calendulacea*.

18. A process for preparing a water-miscible alcohol/1-butanol extract of plant tissues, the plant tissues comprising leaves of a plant selected from the group of plant genera consisting of Wedelia, Eclipta and Aspilia, comprising the following steps:
   (a) defatting the plant tissues by extracting the tissues using a defatting solvent;
   (b) extracting the defatted plant tissues with a solvent consisting essentially of from about 50% to about 100% of a water-miscible alcohol and from 0% to about 50% water;
   (c) evaporating substantially all of the alcohol from the extract;
   (d) optionally adding water to the extract, if needed to provide an aqueous solution;
   (e) extracting the aqueous solution with 1-butanol, thus obtaining a 1-butanol phase and an aqueous phase;
   (f) separating the 1-butanol phase from the aqueous phase; and
   (g) optionally drying the 1-butanol phase.

19. The process of claim 18 wherein the plant species is *W. calendulacea*.

20. The process of claim 19 wherein the water-miscible alcohol is methanol.

* * * * *

UNITED STATES PATENT AND TRADEMARK OFFICE
CERTIFICATE OF CORRECTION

PATENT NO. : 5,130,133

DATED : July 14, 1992

INVENTOR(S) : Tuticorin G. Rajagopalan and Jared L. Randall

It is certified that error appears in the above-identified patent and that said Letters Patent is hereby corrected as shown below:

Column 3, line 29, "E. prostrate" should be --E. prostrata--.

Column 3, line 32, "W. ispida" should be --W. hispida".

Column 4, line 27, "(p<0.05=significantly different)" should be
   --(p 0.05=significantly different)--.

Column 6, line 68, "17 1 g" should be --17.1 g--.

Column 11, line 44, "tables" should be --tablets--.

Column 12, line 33, "disordered" should be --disorder--.

Column 12, line 68, insert after "tissues", --(dry basis)--.

Signed and Sealed this

Eleventh Day of January, 1994

Attest:

BRUCE LEHMAN

*Attesting Officer*    Commissioner of Patents and Trademarks